United States Patent [19]
Seliktar et al.

[11] Patent Number: 5,928,945
[45] Date of Patent: Jul. 27, 1999

[54] APPLICATION OF SHEAR FLOW STRESS TO CHONDROCYTES OR CHONDROCYTE STEM CELLS TO PRODUCE CARTILAGE

[75] Inventors: Dror Seliktar, Atlanta, Ga.; Noushin Dunkelman, San Diego, Calif.; Alvin Edward Peterson, Jamul, Calif.; Ronda Elizabeth Schreiber, Ramona, Calif.; Jane Willoughby; Gail K. Naughton, both of Del Mar, Calif.

[73] Assignee: Advanced Tissue Sciences, Inc., La Jolla, Calif.

[21] Appl. No.: 08/753,104

[22] Filed: Nov. 20, 1996

[51] Int. Cl.$^6$ .............................. C12N 5/06; C12N 5/08; C12N 11/00; C12N 3/00
[52] U.S. Cl. ..................... 435/395; 424/93.7; 435/289.1; 435/298.2; 435/299.1; 435/366; 435/402; 435/174; 435/176; 435/180
[58] Field of Search ..................................... 435/395, 366, 435/397, 402, 289.1, 298.1, 174, 176, 180; 424/93.7

[56] References Cited

U.S. PATENT DOCUMENTS 5,041,138  8/1991  Vacanti et al. ............................. 623/16

*Primary Examiner*—David M. Naff
*Attorney, Agent, or Firm*—Pennie & Edmunds llp

[57] ABSTRACT

Mammalian cells capable of producing cartilage are cultured under a shear flow stress of about 1 to about 100 dynes/cm$^2$ to produce artificial cartilage for surgical transplantation to replace damaged or missing cartilage. Shear flow stressed cells display enhanced maintenance of chondrocyte phenotype and produce an extracellular matrix containing an enhanced ratio of type II collagen to type I collagen. The cells may be chondrocytes, chondrocyte stem cells or cells such as myoblasts or fibroblasts that transdifferentiate into chondrocytes. A bioreactor is used containing a growth chamber having a substrate on which the cells capable of producing cartilage are attached, and means for applying relative movement between a liquid culture medium and the substrate to provide the shear flow stress. The substrate may be a scaffold, or a nonporous surface such as the surface of a rotatable drum or disc, or the surface of a static plate that supports cell growth in a monolayer. Cartilage is produced by covering the substrate with a liquid growth medium, inoculating into the medium cells capable of producing cartilage, allowing the cells to attach to the substrate, applying and maintaining relative movement between the growth medium and the cells to provide the shear flow stress to produce shear flow stressed cells, and culturing the shear flow stressed cells to produce cartilage.

24 Claims, 4 Drawing Sheets

APPLICATION OF SHEAR FLOW STRESS TO CHONDROCYTES OR CHONDROCYTE STEM CELLS TO PRODUCE CARTILAGE

FIELD OF THE INVENTION

This invention relates to mammalian tissue culture and artificial cartilage.

BACKGROUND OF THE INVENTION

Cartilage enables joints to move smoothly. Cartilage consists essentially of highly specialized cells know as chondrocytes, surrounded by a dense extracellular matrix (ECM). In the case of articular cartilage, the tissue is formed primarily from type II collagen, proteoglycans, and water. Fully matured cartilage has a limited capacity for regrowth and repair in response to damage from trauma or degenerative joint disease. Surgical procedures have been developed for replacement of damaged cartilage with cartilage grown in tissue culture. Bioreactors are used to grow cultured cells, e.g., chondrocytes, for use in generating tissue-engineered cartilage.

SUMMARY OF THE INVENTION

We have discovered that cultured chondrocytes do not align under shear flow stress. We have also discovered that application of shear flow stress to cultured chondrocytes enhances maintenance of chondrocyte phenotype. This is reflected by enhanced type II collagen deposition in the chondrocytes.

Based on these discoveries, the invention features a bioreactor for producing artificial cartilage. The bioreactor includes a growth chamber for housing cultured mammalian cells, a substrate for attachment of the cells, and means for applying shear flow stress. The bioreactor applies shear flow stress at a level between about 1 and about 100 dynes/cm$^2$, and preferably, it can apply shear flow stress at a level between about 1 and about 50 dynes/cm$^2$. In some embodiments of the invention, the shear flow stress is applied by means of a reservoir, a pump, and interconnecting tubing. These components are arranged to allow continuous flow of liquid growth medium from the reservoir, through the growth chamber, and back to the reservoir, in response to force applied by the pump.

The substrate in the bioreactor can be a scaffold that supports the growth of a 3-dimensional cell culture. The scaffold can be bioabsorbable. Alternatively, the substrate can be a nonporous surface that supports the growth of cultured cells in a monolayer. The nonporous surface can be the smooth surface of a rotatable drum, a rotatable disc, or a static plate. When a drum or disc is used, shear flow stress is generated by movement, i.e., rotation, of the drum or disc through the liquid culture medium. When a static plate is used, shear flow stress is generated by movement of the liquid culture medium past the plate under force from a pump.

The invention also provides a method for producing artificial cartilage. The method includes the steps of: (a) providing a growth chamber containing a substrate for attachment of cells; (b) bathing the substrate with a liquid growth medium; (c) inoculating into the medium chondrocytes, chondrocyte stem cells, or cells that transdifferentiate into a chondrocyte phenotype; (d) allowing the cells to attach to the substrate; (e) applying and maintaining shear flow stress between about 1 and about 100 dynes/cm$^2$ to the cells, preferably between about 1 and about 50 dynes/cm$^2$; and (f) culturing the shear flow stressed cells for a time sufficient to produce artificial cartilage.

The substrate can be a scaffold, and the scaffold can be bioabsorbable. The substrate can also be a nonporous surface such as a rotatable drum, a rotatable disk, or a static plate.

The shear flow stressed cells grown according to this method display enhanced maintenance of a chondrocyte phenotype. In addition, they produce an extracellular matrix containing an increased ratio of type II collagen to type I collagen.

The invention also provides a method for inducing differentiation of stem cells into chondrocytes. The stem cell differentiation method includes the steps of: (a) providing a growth chamber containing a substrate for the attachment of cells; (b) bathing the substrate with a liquid growth medium; (c) inoculating into the medium mammalian stem cells; (d) allowing the stem cells to attach to the substrate; (e) applying and maintaining shear flow stress between about 1 and about 100 dynes/cm$^2$, preferably between about 1 and about 50 dynes/cm$^2$ to the stem cells; and (f) culturing the stem cells for a time sufficient to allow them to differentiate into chondrocytes.

The invention also features a method for inducing transdifferentiation of cultured cells into chondrocytes. The transdifferentiation method comprises the steps of: (a) providing a growth chamber containing a substrate for attachment of cells; (b) bathing the substrate with a liquid growth medium; (c) inoculating into the medium mammalian cells other than chondrocytes or chondrocyte stem cells; (d) allowing the cells to attach to the substrate; (e) applying and maintaining shear flow stress between about 1 and about 100 dynes/cm$^2$, preferably between about 1 and about 50 dynes/cm$^2$, to the cells; and (f) culturing the cells for a time sufficient to allow them to transdifferentiate into chondrocytes. Preferred nonchondrocyte cell types for use in this transdifferentiation method are fibroblasts and myocytes.

As used herein, "bioabsorbable" means biodegradable in cell culture or in the body of an artificial cartilage transplant recipient.

As used herein, "chondrocyte" means a cartilage cell. Chondrocytes are found in various types of cartilage, e.g., articular (or hyaline) cartilage, elastic cartilage, and fibrocartilage.

As used herein, "substrate" means a supporting structure to which cultured cells anchor or attach, in a growth chamber.

As used herein, "scaffold" means a 3-dimensional, porous, cell culture-compatible structure, throughout which cultured mammalian cells can attach so as to form a 3-dimensional culture. As the terms are used herein, a scaffold is a type of substrate.

As used herein, "shear flow stress" means a fluid borne force acting on cultured cells due to relative movement between a liquid culture medium and the cells. Shear flow stress can be generated by moving liquid past static cells, moving cells through static liquid, or by moving the liquid and the cells simultaneously. Shear flow stress is generally quantified in terms of dynes/cm$^2$.

As used herein, "stem cell" means an undifferentiated cell which generates daughter cells that will mature into the specialized cells characterizing a particular tissue.

As used herein, "transdifferentiation" means the change of a differentiated cell from one phenotype, e.g., myoblast or fibroblast, into another phenotype, e.g., a chondrocyte.

Unless otherwise defined, all technical and scientific terms used herein have the same meaning as commonly understood by one skilled in the art of cell culturing techniques. Although materials and methods similar or equivalent to those described herein can be used in the practice or testing of the invention, the preferred methods and materials are described below. All publications, patent applications, patents and other references mentioned herein are incorporated by reference. In addition, the materials, methods, and examples are illustrative only and not intended to be limiting.

Other advantages and features of the invention will be apparent from the detailed description, and from the claims.

DETAILED DESCRIPTION

Figure 1:
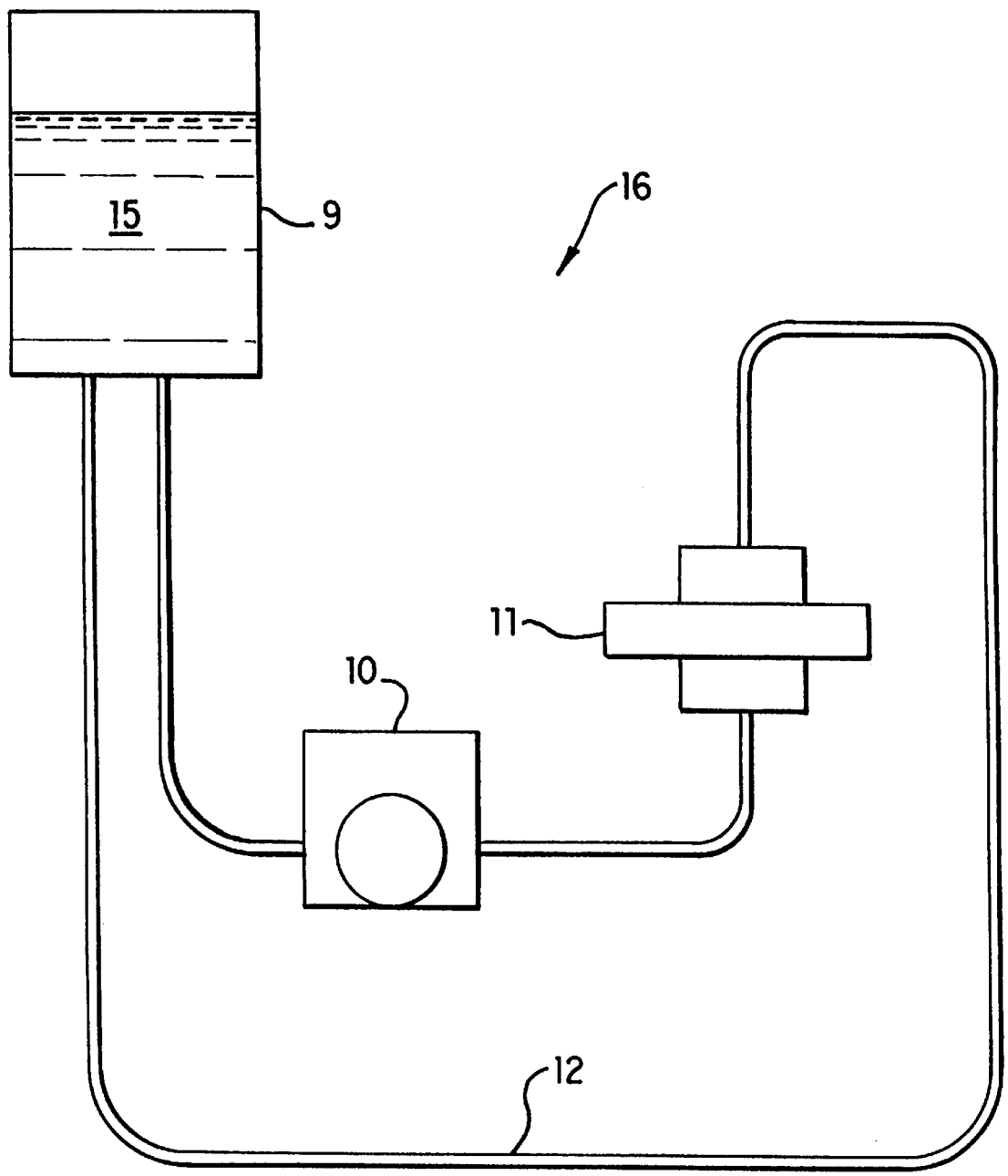
FIG. 1 is a diagrammatic representation of a shear flow bioreactor system that includes a growth chamber, a pump, a media reservoir, and connective tubing.

The present invention provides apparatuses and methods for applying shear flow stress to mammalian cell cultures used for artificial cartilage production.

Applying shear flow stress to a three-dimensional or monolayer chondrocyte culture advantageously increases the ratio of type II to type I collagen produced by the chondrocytes. The shear flow stress also advantageously enhances maintenance of the chondrocyte phenotype. Thus, application of shear flow stress according to this invention improves the functional outcome of a three-dimensional or monolayer chondrocyte culture and increases the useful lifetime of the monolayer culture.

Applying shear flow stress to stem cells induces or promotes differentiation of the stem cells into chondrocytes. Inducing or promoting stem cells to differentiate into chondrocytes is accomplished by substituting stem cells for chondrocytes in the shear flow method described herein with regard to chondrocytes. The chondrocytes arising from the stem cell differentiation process are maintained in the culture, under shear flow stress, for a sufficient time to allow production of artificial cartilage.

Shear flow stress also can be used according to this invention to induce transdifferentiation of differentiated cells into chondrocytes. Transdifferentiation is accomplished by substituting, differentiated cells other than chondrocytes, e.g., myoblasts or fibroblasts, in the shear flow method described herein with regard to chondrocytes. In response to the shear flow stress, the differentiated cells transdifferentiate into chondrocytes. The chondrocytes arising from the transdifferentiation process are maintained in the culture, under shear flow stress, for a sufficient time to allow production of artificial cartilage.

Artificial cartilage produced according to any embodiment of this invention can be used for surgical transplantation, according to established medical procedures, to replace damaged or missing cartilage. Typically, artificial cartilage is employed in the repair of human joints, e.g., knees and elbows.

In the apparatuses and methods of this invention, shear flow stress can be applied to the cultured cells by various means. For example, shear flow stress can be applied by growing a chondrocyte monolayer on the surface of a rotating drum or rotating disc immersed in liquid growth medium. Alternatively, shear flow stress can be applied by growing a chondrocyte monolayer on static plates past which liquid growth medium is pumped. Shear flow stress can also be applied to a 3-dimensional chondrocyte culture by establishing the culture in a chamber through which liquid growth medium is pumped.

The amount of shear flow stress applied to the chondrocytes is controlled by adjusting the rate of rotation of the drum or disc, or adjusting the liquid medium pumping rate. In this invention, the level of shear flow stress applied to the chondrocytes or other cells is between about 1 and about 100 dynes/cm$^2$. Preferably, the shear flow stress is between about 1 and about 50 dynes/cm$^2$. Shear flow stress is calculated according to equation (1):

shear flow stress=$\tau$=6 $\mu$Q/bh$^2$ dynes/cm$^2$ where:
  $\mu$=viscosity of fluid (N sec/m$^2$);
  Q is flow rate (ml/min);
  b=chamber width (cm); and
  h=chamber height (cm).

Cultured Chondrocytes

Preferably, the cultured chondrocytes are anchored, i.e., attached, to a substrate, whether grown as a monolayer or grown in a 3-dimensional culture. A monolayer-supporting surface, or a 3-dimensional scaffold, in a bioreactor is inoculated with chondrocytes, stem cells, or differentiated cells suitable for transdifferentiation. Artificial cartilage can be produced by growing chondrocytes in a conventional mammalian tissue culture medium, e.g., RPMI 1640, Fisher's, Iscove's or Mccoy's. Such media are well known in the art, and are commercially available. Typically, the cells are cultured at 37° C. in air supplemented with 5% $CO_2$. Under these conditions, a chondrocyte monolayer or a three dimensional cartilage matrix is produced in approximately 7 to 56 days, depending on the cell type used for inoculation and the culture conditions.

Isolated chondrocytes can be used to inoculate the reactor surface or 3-dimensional matrix. Alternately, stem cells, or cells suitable for transdifferentiation can be used for inoculation.

Cells used for inoculation of cultures used in the present invention can be isolated by any suitable method. Various starting materials and methods for chondrocyte isolation are known. See generally, Freshney, *Culture of Animal Cells. A Manual of Basic Techniques,* 2d ed., A. R. Liss Inc., New York, pp 137–168 (1987). Examples of starting materials for chondrocyte isolation include mammalian knee joints or rib cages.

If the starting material is a tissue in which chondrocytes are essentially the only cell type present, e.g., articular cartilage, the cells can be obtained directly by conventional collagenase digestion and tissue culture methods. Alternatively, the cells can be isolated from other cell types present in the starting material. One known method for chondrocyte isolation includes differential adhesion to plastic tissue culture vessels. In a second method, antibodies that bind to chondrocyte cell surface markers can be coated on tissue culture plates and then used to selectively bind chondrocytes from a heterogeneous cell population. In a third method, fluorescence activated cell sorting (FACS) using chondrocyte-specific antibodies is used to isolate chondrocytes. In a fourth method, chondrocytes are isolated on the basis of their buoyant density, by centrifugation through a density gradient such as Ficoll.

Examples of tissues from which stem cells for differentiation, or differentiated cells suitable for transdifferentiation, can be isolated include placenta, umbilical cord, bone marrow, skin, muscle, periosteum, or perichondrium. Cells can be isolated from these tissues by explant culture and/or enzymatic digestion of surrounding matrix using conventional methods.

When the artificial cartilage construct has grown to the desired size and composition, a cryopreservative fluid can be introduced into the system. The cryopreservative fluid freezes the artificial cartilage construct for future use. Cryopreservation methods and materials for mammalian tissue culture material are known to those of ordinary skill in the art.

Bioreactor Flow System

In some embodiments of this invention, as shown in FIG. 1, a circulating flow system 16 is used with a growth chamber 11. The circulating flow system 16 includes a media reservoir 9, a pump 10, a growth chamber 11, and tubing 12.

Any sterilizable liquid container can be adapted for use as a reservoir 9. One type of preferred reservoir is a sterile bag. Suitable sterile bags are commercially available, e.g., from Gibco/BRL. In some embodiments of the invention, an upper reservoir is placed upstream of the bioreactor, a lower reservoir is placed downstream of the bioreactor, and the pump returns liquid medium from the lower reservoir to the upper reservoir.

The reservoir 9 can include a sterile filter to provide a direct source of sterile gas to the liquid in the system. Alternatively, the reservoir 9 can include gas permeable tubing or membranes made of silicone or Teflon, e.g., to provide an indirect source of sterile gas to the system via diffusion. Preferably, one or more valves and a flow meter are included in the flow system.

The pump 10 is designed to transfer liquid from the reservoir 9 to the growth chamber 11, and return it, under sterile conditions. Typically, the pump 10 controls both the flow rate and pressure within the system. The pump 10 can be a peristaltic pump. Alternatively, an elastomeric bladder with an alternating pressure source can be used. Varying the external pressure causes the bladder to inflate and deflate. A pair of check valves can be used to achieve unidirectional movement of sterile fluid in the system.

The connective tubing 12 for circulating the sterile liquid within the system can be stainless steel pipe, or durable medical-grade plastic tubing. Alternatively, the tubing 12 can be a gas-permeable material such as silicone.

3-Dimensional Cultures

Methods and materials for 3-dimensional cultures of mammalian cells are known in the art. See, e.g., U.S. Pat. No. 5,266,480. Typically, a scaffold is used in a bioreactor growth chamber to support a 3-dimensional culture. The scaffold can be made of any porous, tissue culture-compatible material into which cultured mammalian cells can enter and attach or anchor. Such materials include nylon (polyamides), dacron (polyesters), polystyrene, polypropylene, polyacrylates, polyvinyl chloride, polytetrafluoroethylene (teflon), nitrocellulose, and cotton. Preferably, the scaffold is a bioabsorbable or biodegradable material such as polyglycolic acid, catgut suture material, or gelatin. In general, the shape of the scaffold is not critical.

Optionally, prior to inoculating chondrocytes into the scaffold, stromal cells are inoculated into the scaffold and allowed to form a stromal matrix. The chondrocytes are then inoculated into the stromal matrix. The stromal cells can include fibroblasts. The stromal cells can also include other cell types.

A 3-dimensional culture can be used in a circulating flow system 16 such as that depicted schematically in FIG. 1. Shear flow stress is applied to the chondrocytes by the movement of liquid culture medium pumped through the growth chamber, which contains the 3-dimensional culture. Preferably, the scaffold and attached cells are static.

Data obtained from two bioreactor systems, Apollo and Gemini I, show that increasing flow rates i.e., increasing shear stress, improves chondrocyte performance in 3-dimensional cultures used to produce artificial cartilage.

Apollo Bioreactor

Articular cartilage was aseptically harvested from the femoral/tibial joints of skeletally mature New Zealand white rabbits within 4 hr post-sacrifice. Chondrocytes were isolated by collagenase digestion as described by Dunkelman et al. (*Biotech. Bioengineering* 46: 299–305 (1995)). They were then grown for two passages in culture medium (DMEM containing 10% fetal bovine serum, 2 mM L-glutamine, 2 mM nonessential amino acids, 50 mg/mL proline, 1 mM sodium pyruvate, and 35 mg/mL gentamycin).

Injection molded, polycarbonate bioreactors (1.2 mL internal volume) were assembled using gas permeable silicone and bioprene tubing and sterilized by electron-beam radiation (2.5 Mrad). Polyglycolic acid (PGA) mesh (52 mg/cc, non-heat plated, 1.9 mm thick, 1 cm diameter, porosity 97% void volume) were sterilized by ethylene oxide gas and stored under nitrogen until use. The sterile PGA mesh were presoaked in culture medium overnight at 37° C. and placed in sterile bioreactor systems.

The mesh were seeded using a recirculating seeding technique in which each bioreactor system (5 tandem bioreactors) was attached to a media bag containing a cell suspension of $30 \times 10^6$ cells in 35 mL of culture medium. The system was connected to a pump (Cole-Parmer) to obtain a culture medium flow rate of 0.2 mL/min, and placed in a humidified incubator at 37° C. After seeding, constructs were cultured with media containing ascorbate (50 µg/mL), at a flow rate of 0.05 mL/min. After overnight incubation, the flow rate increased to 0.2 mL/min, then weekly in increments of 0.2 mL/min. Flow direction changed 5 days per week.

After two or four weeks of culture, the cartilage constructs were analyzed for total sulfated glycosasinoglycans (GAGs) by dimethylmethylene blue binding as described by Farndale et al. (*Biochem. Biophys. Acta* 883: 173–177 (1986)). Total collagen was analyzed by hydroxyproline quantification as described by Woessner et al. (Arch. Biochem. Biophys. 93: 440–447 (1961)). Separate samples were harvested, fixed in 10% buffered formalin, and paraffin embedded. Five micron sample sections were stained with Safranin O or collagen antibodies (Southern Biotech, Birmingham, Ala.) to assess the quantity and distribution of sulfated glycosaminoglycans (GAG) and collagen types, respectively.

Figure 5:
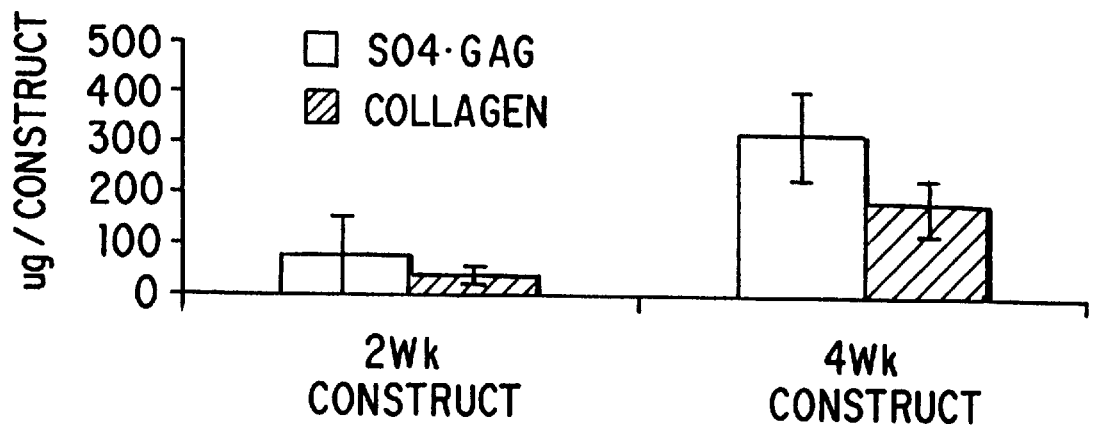
FIG. 5 is a bar graph summarizing data on collagen and sulfated GAG levels in artificial cartilage constructs at two weeks and four weeks. White bars, sulfated GAG; black bars, collagen.
Figure 6:
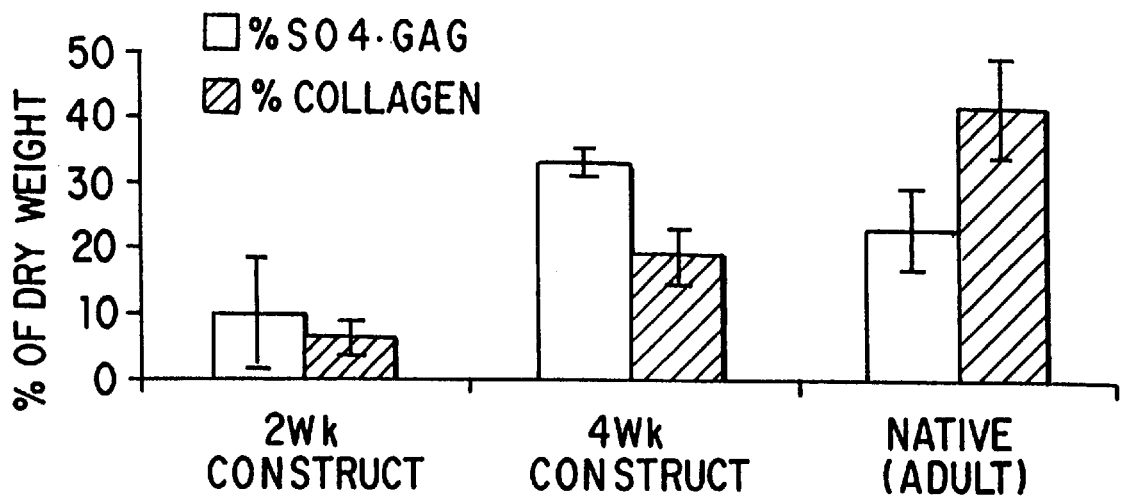
FIG. 6 is a bar graph summarizing data on collagen and sulfated GAG levels in artificial cartilage constructs at two weeks, four weeks, and in native cartilage. White bars, sulfated GAG; black bars, collagen.

Between two and four weeks of culture in hydrodynamic conditions, a significant increase (p<0.05) in the levels, as well as the percentage of collagen and sulfated-GAG on the cartilage constructs was observed (FIGS. 5 and 6). At four weeks, the concentrations were not significantly different than those in adult rabbit articular cartilage (FIG. 6). Although collagen levels increased between two and four weeks of culture, at four weeks the collagen content was still below that of rabbit articular cartilage. In comparison to these hydrodynamically grown constructs less collagen and sulfated-GAG was present in cultures held statically for the same time periods.

Histologically, the pattern of sulfated-GAG deposited on constructs grown under hydrodynamic conditions was similar to that of native rabbit articular cartilage, while that of statically grown constructs was non-uniform, with little sulfated-GAG in the construct's center. Type II collagen was present in immunostained constructs with a similar distribution to that seen in native articular cartilage. Lacunas surrounded the majority of cells in hydrodynamically but not statically held constructs.

Gemini I Bioreactor

Similar results were obtained in experiments carried out using a scaled up bioreactor. Rabbit chondrocytes were seeded at 30 $E^6$ cells/system, and either grown at 0.05 ml/min constant flow rate, or at a flow rate gradually increased from 0.05 to 0.8 ml/min. The cell grown under the increased flow rate showed higher matrix deposition. In cultures grown at the increased flow rate, glycosaminoglycan (GAG) levels were from 25% to 50%, whereas in comparable cells grown at the low flow rate (0.05 ml/min), GAG levels were approximately 3%. In cultures grown at the increased flow rate, collagen levels were from 12% to 20%, whereas in comparable cells grown at the low flow rate (0.05 ml/min), collagen levels were approximately 5%.

Monolayer Cultures

Bioreactors can be designed in a number of ways to produce shear flow stress on a chondrocyte monolayer. This induces and maintains the chondrocyte phenotype.

Figure 2:
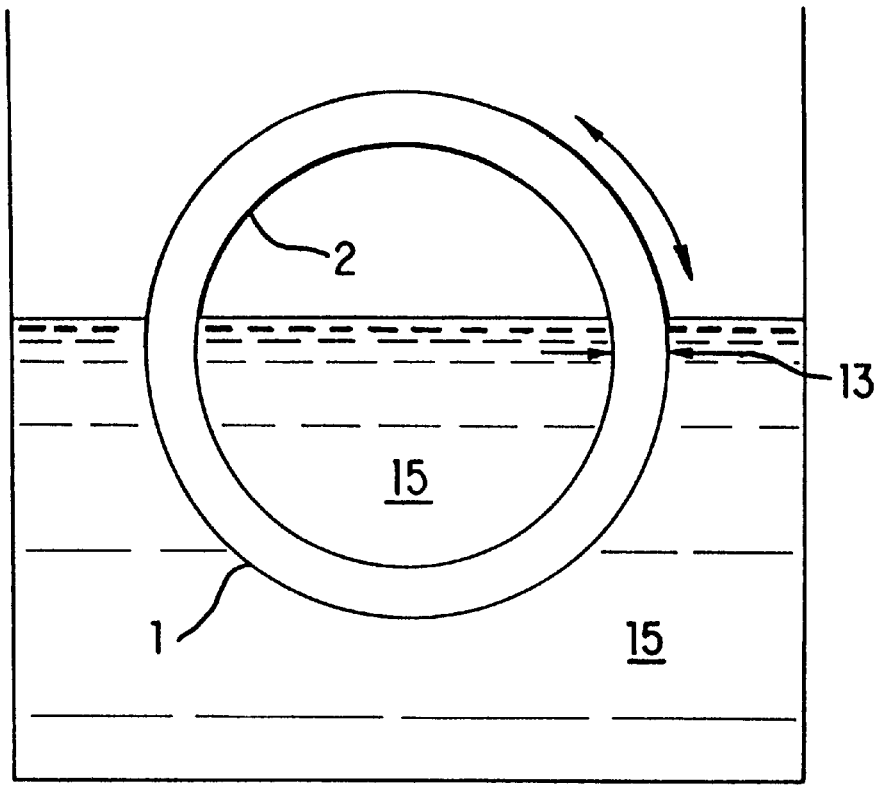
FIG. 2 is a diagrammatic representation of a shear flow growth chamber that contains concentric inner and outer drums at least partially submerged in liquid culture medium.

FIG. 2 schematically illustrates a shear flow growth chamber 3 that includes concentric drums 1, 2. The surface of either drum 1,2, or both, can serve as a substrate for the attachment of cells. One of the drums can remain stationary while the other drum rotates. Alternatively, both drums can rotate. In either arrangement, the drums 1, 2 are at least partially submerged in liquid growth medium 15. The relative movement between the drum-anchored cells and the liquid growth medium 15 generates shear flow stress.

The amount of flow stress applied to the cells can be adjusted by adjusting drum rotation speed according to equation (1) above. The distance 13 between the drums 1, 2 is parameter (h) in equation (1). Preferably, drum rotation speed is selected to achieve a shear flow stress from about 1 to about 100 dynes/cm$^2$, and more preferably from about 1 to about 50 dynes/cm$^2$. Preferably, the drum is rotated by means of a variable speed electric motor. The optimal distance between the two drums depends on various factors, including the drum size and the material from which they are made. Determination of the optimal drum configuration is within ordinary skill in the art. Because shear flow stress is generated by the drum's rotation, a continuous flow arrangement involving a liquid reservoir and pump is optional.

Figure 3:
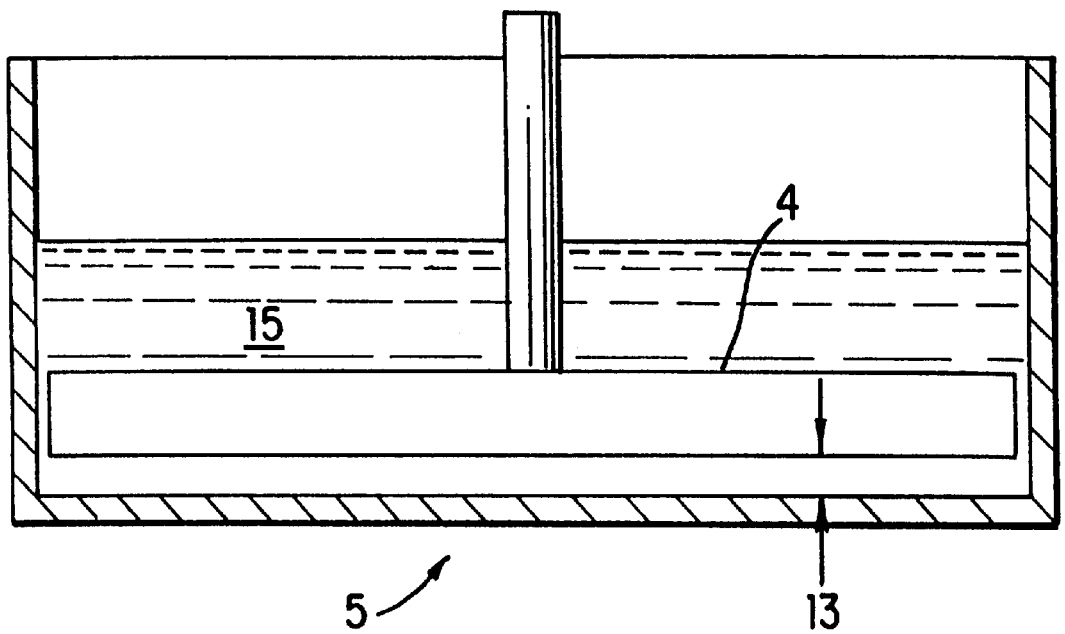
FIG. 3 is a diagrammatic representation of a shear flow growth chamber that contains a disk that rotates within the growth chamber.

FIG. 3 schematically illustrates a shear flow growth chamber 5 that includes a rotating disc 4 in the growth chamber 5. The disc 4 is immersed in liquid culture medium 15, where it serves as a substrate for attachment of cells. The amount of flow stress applied to the cells can be adjusted by adjusting disc rotation speed according to equation (1) above. The distance 13 between the disk 4 and the growth chamber wall is parameter (h) in equation (1). Preferably, disc rotation speed is selected to achieve a shear flow stress from about 1 to about 100 dynes/cm$^2$, and more preferably from about 1 to about 50 dynes/cm$^2$. Optionally, a multiplicity of discs can be placed on a single rotating shaft to increase the total surface area available to support cell attachment and growth. Typically, the disc is rotated by means of a variable speed electric motor. Because shear flow stress is generated by the disc rotation, a continuous flow arrangement involving a liquid reservoir and pump is optional.

Cells located near the periphery of the rotating disc move at a greater speed than cells located near the central shaft. Therefore, they are subjected to a greater shear flow stress. The magnitude of this effect depends on disc size. Thus, the rotating disc embodiment of the invention permits simultaneous growth of cells exposed to a continuous range of shear flow stress levels within a single bioreactor. This feature can be exploited for systematic comparison of the effect of varying shear flow stress levels on a given type of cell in a given culture medium.

Figure 4:
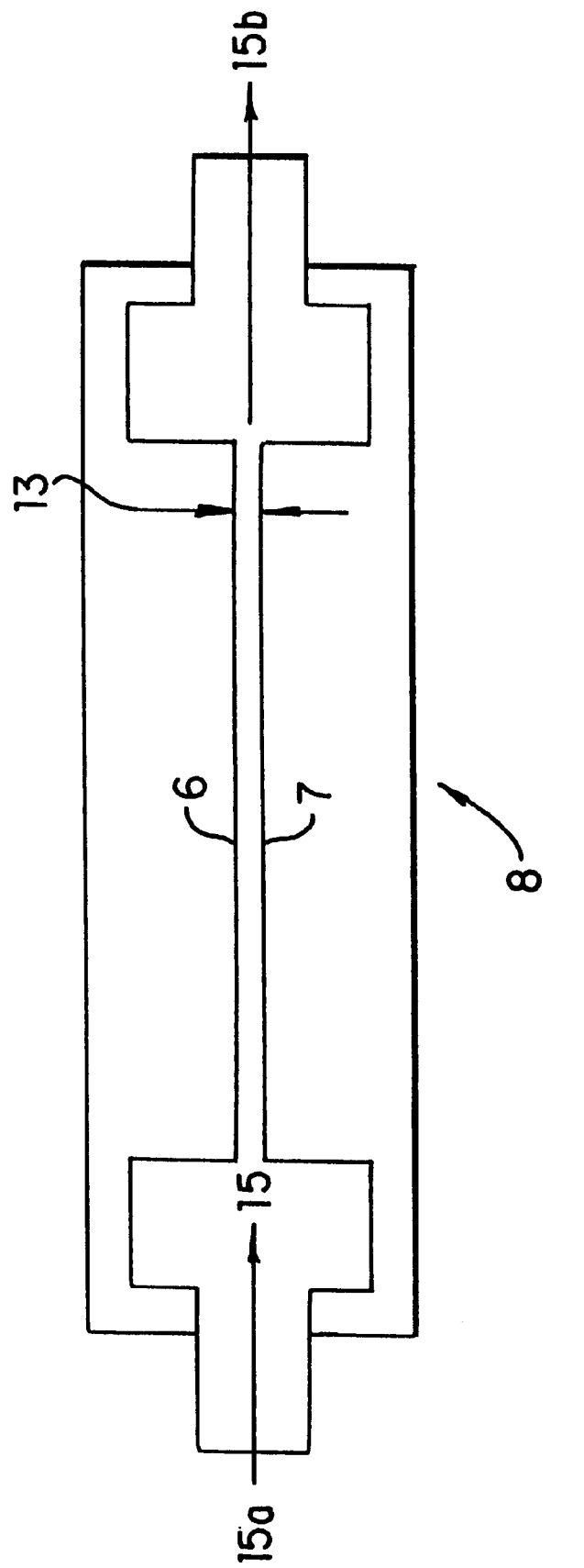
FIG. 4 is a diagrammatic representation of a shear flow growth chamber that contains static parallel plates inside the growth chamber.

FIG. 4 schematically illustrates a shear flow growth chamber 8 that includes two parallel, static plates or walls 6 and 7 inside the growth chamber 8. A single pair of static plates 6, 7 can be used, or more than one pair can be used in the same growth chamber 8. Because the plates 6, 7 are static, shear flow stress is generated solely by the movement of liquid culture medium 15 pumped through the chamber 8. The liquid culture medium 15 is pumped past the parallel plates 6 and 7, to create a shear flow stress between about 1 and about 100 dynes/cm$^2$, and preferably between about 1 and about 50 dynes/cm$^2$. Shear flow stress is adjusted by adjusting liquid culture medium 15 flow rate in accordance with equation (1) above. The distance 13 between the static plates 6, 7 is parameter (h) in equation (1). The static plates 6, 7 are preferably parallel to each other, and at right angles to the prevailing flow of liquid growth medium 15.

The advantage of increasing the number of plates 6, 7 is greater total surface area on which cells can form a monolayer. The potential disadvantage of multiple plates is that as the number of plates increases, it may become relatively more difficult to maintain an even level of shear flow stress on cells throughout the chamber 8. One way of maintaining an even level of shear flow stress is to disperse the entering liquid culture medium 15a over a wide area on one wall of the chamber 8 while collecting the exiting liquid culture medium 15b from a similarly wide area on the opposite wall of the chamber.

The rotating drums 1, 2, rotating disc 4, or static plates 6, 7 must be made of a tissue culture compatible material. Various tissue culture compatible materials are known, e.g., polystyrene, polycarbonate, and stainless steel. Selection of a suitable material for the walls of the growth chamber and the monolayer-supporting substrate is within ordinary skill in the art.

In experiments described below, liquid flow rate in a bioreactor was adjusted to obtain preselected shear flow stress levels of approximately 1 dyne/cm$^2$ and approximately 24 dynes/cm$^2$. Viscosity ($\mu$) of the liquid culture medium was 0.0012N sec/m$^2$; chamber width (b) was 2.5 cm; and chamber height (h) was 0.025 cm. Using equation (1) above, it was calculated that for a shear flow stress of 1 dyne/cm$^2$, flow rate (Q) should be 1.3 ml/min. It was calculated that for a shear flow stress of 24 dynes/cm$^2$, flow rate (Q) should be 31.25 ml/min.

For seeding of chondrocytes, plates (7.5 cm by 3.75 cm) were cut from large tissue culture dishes. The plates were sterilized by treatment with 70% ethanol, followed by a 1-hour treatment with ultraviolet light in a laminar flow hood. The plates were then placed in petri dishes and plated with a 1 ml suspension of passage 2 rabbit chondrocytes, at a density of approximately 100,000 cells per plate. Cell culture medium used in this procedure was complete medium without ascorbate. The plates were covered in medium and allowed to stand for 6 hours. They were then transferred to an incubator for 2 days at 37° C. Approximately 15 ml of additional medium was added, and the plates were placed in the flow loop. At this stage, the cells were subconfluent.

Experiments were carried out to compare results obtained at low and high flow rates in this system. A low flow rate, which generated 1 dyne/cm$^2$, was used with chondrocytes at a density comparable to the density used in a shear stress roller bottle apparatus operating at 1 rpm. A high flow rate, which generated 24 dynes/cm$^2$ was also tested, for comparison.

The results demonstrated a shear flow stress-dependent difference in chondrocyte collagen production. At 24 dynes/cm$^2$, production of type I collagen was diminished, in comparison to the static roller bottle results. At 24 dynes/cm$^2$, production of type II collagen was enhanced, in comparison to the static roller bottle results. Under the shear stress conditions in these experiments, there was no orientation of the cells in the direction of flow.

Other embodiments are within the following claims.

We claim:

1. A bioreactor for producing cartilage comprising a growth chamber, a substrate on which chondrocyte cells or chondrocyte stem cells are attached, and means for applying relative movement between a liquid culture medium and the substrate to provide a shear flow stress of about 1 to about 100 dynes/cm$^2$ to the cells attached to said substrate.

2. The bioreactor of claim 1, further comprising a means for applying shear flow stress of about 1 to about 50 dynes/cm$^2$.

3. The bioreactor of claim 1, wherein said means for applying shear flow stress comprises a reservoir, a pump, and tubing interconnecting said growth chamber, said reservoir, and said pump, so as to allow continuous flow of liquid growth medium from said reservoir, through said growth chamber, and back to said reservoir, in response to force applied by said pump.

4. The bioreactor of claim 1, wherein said substrate is a scaffold.

5. The bioreactor of claim 4, wherein said scaffold is bioabsorbable.

6. The bioreactor of claim 1, wherein said substrate is a nonporous surface that supports the growth of said cells in a monolayer.

7. The bioreactor of claim 6, wherein said nonporous surface is the surface of a rotatable drum.

8. The bioreactor of claim 6, wherein said nonporous surface is the surface of a rotatable disc.

9. The bioreactor of claim 6, wherein said nonporous surface is a static plate.

10. The bioreactor of claim 4, wherein the scaffold is biocompatible.

11. The bioreactor of claim 10, wherein the scaffold is biodegradable.

12. The bioreactor of claim 10, wherein the scaffold is non-biodegradable.

13. A method for producing cartilage, said method comprising the steps of:

(a) providing a growth chamber comprising a substrate for cell attachment;

(b) covering said substrate with a liquid growth medium;

(c) inoculating chondrocyte cells or chondrocyte stem cells into said medium;

(d) allowing said cells to attach to said substrate;

(e) applying and maintaining relative movement between the liquid growth medium and the cells attached to the substrate to provide a shear flow stress of about 1 to about 100 dynes/cm$^2$ to said cells, thereby producing shear flow stressed cells; and (f) culturing said shear flow stressed cells for a time sufficient to produce cartilage.

14. The method of claim 13, wherein said shear flow stress is about 1 to about 50 dynes/cm$^2$.

15. The method of claim 13, wherein said substrate is a scaffold.

16. The method of claim 15, wherein said scaffold is bioabsorbable.

17. The method of claim 13, wherein said substrate is a nonporous surface that supports the growth of said cells in a monolayer.

18. The method of claim 17, wherein said nonporous surface is the surface of a rotatable drum.

19. The method of claim 17, wherein said nonporous surface is the surface of a rotatable disc.

20. The method of claim 17, wherein said nonporous surface is a static plate.

21. The method of claim 13, wherein said shear flow stressed cells:

(a) display enhanced maintenance of a chondrocyte phenotype; and (b) produce an extracellular matrix containing an enhanced ratio of type II collagen to type I collagen.

22. The method of claim 15, wherein the scaffold is biocompatible.

23. The method of claim 22, wherein the scaffold is biodegradable.

24. The method of claim 22, wherein the scaffold is non-biodegradable.

* * * * *